United States Patent
Mentak

(12)
(10) Patent No.: US 6,635,731 B2
(45) Date of Patent: Oct. 21, 2003

(54) WATER PLASTICIZED HIGH REFRACTIVE INDEX POLYMER FOR OPHTHALMIC APPLICATIONS

(75) Inventor: Khalid Mentak, Goleta, CA (US)

(73) Assignee: Surgidev Corporation, Goleta, CA (US)

( * ) Notice: Subject to any disclaimer, the term of this patent is extended or adjusted under 35 U.S.C. 154(b) by 0 days.

(21) Appl. No.: 09/918,000

(22) Filed: Jul. 30, 2001

(65) Prior Publication Data

US 2002/0007032 A1 Jan. 17, 2002

Related U.S. Application Data

(62) Division of application No. 09/358,757, filed on Jul. 22, 1999, now Pat. No. 6,281,319.
(60) Provisional application No. 60/128,751, filed on Apr. 12, 1999.

(51) Int. Cl.⁷ ............................ C08F 118/02; A61F 2/16
(52) U.S. Cl. ...................... 526/319; 526/320; 526/323; 526/323.2; 526/326; 526/327; 526/328.5; 526/346; 526/347; 623/6.11; 623/6.12; 623/6.58
(58) Field of Search ................................. 526/319, 320, 526/323, 323.2, 327, 328.5, 346, 347, 326; 623/6.58, 6.12, 6.36, 6.11

(56) References Cited

U.S. PATENT DOCUMENTS

| | | | |
|---|---|---|---|
| 3,513,224 A | * 5/1970 | Sherr .......................... 260/872 |
| 4,228,269 A | 10/1980 | Loshaek et al. |
| 4,528,301 A | 7/1985 | Upchurch et al. |
| 4,619,662 A | 10/1986 | Juergens, Jr. .................. 623/6 |
| 4,731,079 A | * 3/1988 | Stoy ............................ 206/5.1 |
| 4,834,750 A | 5/1989 | Gupta ........................... 623/6 |
| 5,093,408 A | 3/1992 | Jung et al. |
| 5,132,384 A | 7/1992 | Matsuda et al. |
| 5,217,491 A | 6/1993 | Vanderbilt .................... 623/6 |
| 5,290,892 A | 3/1994 | Namdaran et al. .......... 526/259 |
| 5,319,007 A | * 6/1994 | Bright ......................... 351/159 |
| 5,326,506 A | 7/1994 | Vanderbilt .................. 264/1.7 |
| 5,331,073 A | 7/1994 | Weinschenk, III et al. . 526/264 |
| 5,359,021 A | 10/1994 | Weinschenk, III et al. . 526/264 |
| 5,433,746 A | 7/1995 | Namdaran et al. ............. 623/6 |
| 5,480,950 A | 1/1996 | Wang et al. |
| 5,693,095 A | 12/1997 | Freeman et al. ................ 623/6 |
| 5,776,191 A | 7/1998 | Mazzocco ...................... 623/6 |
| 6,099,123 A | * 8/2000 | Engardio et al. ............ 264/1.1 |
| 6,150,479 A | 11/2000 | Klemarczyk et al. |
| 6,201,089 B1 | 3/2001 | Carter |
| 6,265,465 B1 | 7/2001 | Benz et al. |
| 6,281,319 B1 | 8/2001 | Mentak |

FOREIGN PATENT DOCUMENTS

| | | |
|---|---|---|
| EP | 0 485 197 A1 | 5/1992 |
| EP | 0 485 197 B1 | 10/1996 |
| GB | 2 171 106 A | 8/1986 |
| WO | WO 97/24382 | 7/1997 |
| WO | WO 00/34804 | 6/2000 |
| WO | WO 01/18078 A1 | 3/2001 |
| WO | WO 01/18079 A1 | 3/2001 |

OTHER PUBLICATIONS http://www.alconlabs.com, Alcon® Laboratories, Inc., "All About Cataracts, The AcrySof® IOL Story", 1996, 2 pages.
Martin, Robert G., James P. Gills and Donald R. Sanders, *Foldable Intraocular Lenses*, Douglas D. Koch, M.D., Ch. 8, pp. 161–177, "Alcon AcrySof™ Acrylic Intraocular Lenses", Slack, Inc., 1993.

* cited by examiner

*Primary Examiner*—Tatyana Zalukaeva
(74) *Attorney, Agent, or Firm*—Michael Best Friedrich LLP; Grady J. Frenchik; Linda Blair Meyer

(57) ABSTRACT

A high refractive index, foldable polymer suitable for use in ophthalmic devices, such as intraocular lenses, is provided. The polymer may be produced from a polymerization reaction of first, second and third monomeric components and a crosslinking agent. The first monomeric component includes an aryl acrylate or an aryl methacrylate. The second monomeric component, which is not an acrylate, includes a monomer having an aromatic ring with a substituent having at least one site of ethylenic unsaturation. The third monomeric component includes a high water content hydrogel-forming monomer. The resulting high refractive index copolymer is durable enough to be cut and polished when dry, and becomes soft and foldable when hydrated.

2 Claims, No Drawings

WATER PLASTICIZED HIGH REFRACTIVE INDEX POLYMER FOR OPHTHALMIC APPLICATIONS

CROSS-REFERENCE TO RELATED APPLICATIONS

This application is a divisional of U.S. patent application Ser. No. 09/358,757, filed on Jul. 22, 1999, now U.S. Pat. No. 6,281,319 which claims priority to U.S. Provisional Patent Application Ser. No. 60/128,751, filed on Apr. 12, 1999.

BACKGROUND OF INVENTION

This invention relates to copolymer materials which are useful as ophthalmic devices, such as contact lenses, intraocular lenses (IOLs), keratoprostheses, and corneal rings or inlays, and a process for making and using such copolymer materials. In particular, this invention relates to intraocular foldable lenses formed from acrylic copolymer materials.

With recent advances in small-incision cataract surgery, increased emphasis has been placed on developing soft, foldable materials suitable for use in artificial ophthalmic lenses. In general, these materials fall into one of three categories: hydrogels, silicones, and generally, others.

The refractive power of a lens is a function of its shape and the refractive index of the material of which it is made. A lens made from a material having a higher refractive index can be thinner and provide the same refractive power as a lens made from a material having a relatively lower refractive index. Thinner lenses are easier to insert and cause less trauma during surgery.

Hydrogel materials are hard or rigid when dry, and absorb a large amount of water (e.g., up to 20–70% by weight) when hydrated, which lowers the refractive index of the material. These materials tend to be brittle when dry, and have poor mechanical properties for ophthalmic applications. In a hydrated state, hydrogel materials become soft and pliable. Known hydrated hydrogels have a relatively low refractive index, for example, less than 1.48. In addition to adversely affecting the refractive index, the absorbed water also significantly increases the diameter and thickness of the IOLs, for example, by as much as about 15 percent.

Silicone materials have a slightly higher refractive index (for example, 1.51), but tend to unfold too rapidly after being placed in the eye in a folded configuration. The biocompatibility of silicone materials may also be a concern.

U.S. Pat. No. 5,290,892 (Namdaran et al.), U.S. Pat. No. 5,331.073 (Weinschenk, III et al.), and U.S. Pat. No. 5,693,095 (Freeman et at.), the complete disclosures of which are hereby incorporated by reference, discuss forming foldable lenses out of a polymer material derived from an ethoxyaryl (meth)acrylate with a crosslinker or with a second acrylate monomer and crosslinker. Since the polymer material is soft/foldable, those patents discuss mold forming the polymer material to individually form the lens. Likewise, U.S. Pat. No. 5,433,746 to Namdaran et al., which is herein fully incorporated by reference, discloses forming flexible intraocular lenses by molding polymeric materials which have a relatively low glass transition temperature. Such molding requires specialized equipment and expensive customized molds. In addition, the resulting molded lenses tend to have poor surface quality since they generally cannot be polished. Alternatively, U.S. Pat. No. 5,331,073 discusses forming lenses from a soft foldable material by machining the lenses at cryogenic temperatures. Such a process is cumbersome and expensive.

A foldable, high refractive index material, which may be machined and polished using conventional technology, would be a significant advancement in the art.

SUMMARY OF THE INVENTION

The present invention provides a foldable, high refractive index material which may be machined using inexpensive conventional lathe cutting techniques, such as those used in the manufacture of polymethyl methacrylate (PMMA) lenses. The polymeric materials are useful for forming ophthalmic devices, particularly intraocular lenses, comprising polymer units derived from at least three different monomeric components. The resulting polymeric materials are also useful for other ophthalmic devices, such as contact lenses, keratoprostheses, intracorneal lenses (ICL), and corneal rings or inlays, as well as for other applications.

A significant novel aspect of polymeric material of the invention is that it both (a) is hard enough to machine at room temperature, and (b) may be rendered foldable through a controlled hydrating process. Further, the IOL may be hydrated to a suitably flexible state with minimal water uptake. The relatively low water uptake allows efficient hydration without affecting mechanical or optical properties and without changing the dimensions or the refractive index of the foldable lens. Another major advantage of the invention is the ability to tumble polish the lenses to provide smooth and rounded edges. This is facilitated, in part, by the relatively high glass transition temperature (Tg) of the material.

One aspect of the present invention is a composition comprising a hydratable copolymer. The copolymer includes:

a) a first monomeric component which is an aryl acrylate or an aryl methacrylate;
b) a second monomeric component which is a monomer having an aromatic ring with a substituent having at least one site of ethylenic unsaturation, wherein the second monomeric component is other than an acrylate; and
c) a third monomeric component which is a high water content hydrogel-forming monomer. Preferably, the copolymer further includes a crosslinking agent.

Another aspect of the invention is an ophthalmic device made from the copolymer of the invention.

The invention also provides a process for making ophthalmic devices such as intraocular lenses from the polymer(s) disclosed. The process generally involves forming a rigid polymer work piece from the copolymer of the invention, forming an ophthalmic device from the work piece, and hydrating the ophthalmic device to a sufficiently soft and flexible state so that, if desired, the device can be folded.

A further aspect of the invention is a method of implanting an ophthalmic device within an eye. The method involves providing a hydratable ophthalmic device which is rigid at room temperature when dry, and foldable at room temperature when hydrated. The ophthalmic device is hydrated and a syringe is provided which contains the hydrated ophthalmic device. The ophthalmic device is then injected into the eye.

DESCRIPTION OF THE PREFERRED EMBODIMENTS

The polymer material of the present invention comprises polymer units derived from the polymerization of first, second, and third monomeric components. These components may include aryl (meth)acrylate monomer, an aromatic monomer, and a high water content hydrogel-forming monomer, respectively. Preferably a crosslinking agent is included. Each of the components is described below in more detail.

The composition may optionally include other monomeric components, an initiator, or an ultraviolet (UV) absorbing material. The proportions of the monomers should preferably be chosen to produce a substantially rigid polymer having a glass transition temperature of at least about normal room temperature. Each of the three different monomeric components is preferably present in the copolymer in an amount of at least about 10 weight percent, more preferably, at least about 20 weight percent. This invention contemplates preparation of random and block copolymers of the monomeric components discussed herein. Unless otherwise stated, all weight percents are based on the total weight of the composition prior to polymerization.

In a highly preferred embodiment, the composition comprises a hydratable copolymer which includes:
a) at least about 20 weight percent of a first monomeric component such as ethylene glycol phenyl ether acrylate or polyethylene glycol phenyl ether acrylate;
b) at least about 10 weight percent of a second monomeric component such as styrene or substituted styrene;
c) at least about 10 weight percent of a third monomeric component such as hydroxy ethyl methacrylate, hydroxyethoxy ethyl methacrylate, or methacrylic acid; and
d) less than about 10 weight percent of a crosslinking agent such as a diacrylate or a dimethacrylate. The resulting copolymer has a refractive index greater than about 1.50 and is foldable at normal room temperature (that is, about 20–25° C.) when hydrated.

Monomers

Generally, the first monomeric component is an aryl acrylate or an aryl methacrylate. These compounds may also be referred to as aryl (meth)acrylate monomers. The term "aryl" implies that the compound contains at least one aromatic group. Such compounds typically correspond to the formula (I):

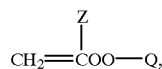

where:
Z is —H or —CH₃, and
Q includes at least one aromatic ring.
Representative substituents Q include, without limitation: ethylene glycol phenyl ether, poly(ethylene glycol phenyl ether acrylate), phenyl, 2-ethylphenoxy, 2-ethylphenoxy, hexylphenoxy, hexylphenoxy, benzyl, 2-phenylethyl, 4-methylphenyl, 4-methylbenzyl, 2-2-methyphenylethyl, 2-3-methylphenylethyl methacrylate, 2-4-methylphenylethyl, 2-(4-propylphenyl)ethyl, 2-(4-(1-methylethyl)pheny)ethyl, 2-(4-methoxyphenyl)ethyl, 2-(4-cyclohexylpheny)ethyl, 2-(2-chlorophenyl)ethyl, 2-(3-chlorophenyl)ethyl, 2-(4-chlorophenyl)ethyl, 2-(4-bromophenyl)ethyl, 2-(3-phenylphenyl)ethyl. 2-(4-phenylphenyl)ethyl), 2-(4-benzylphenyl)ethyl and the like.

Suitable aryl (meth)acrylate monomers include, for example: ethylene glycol phenyl ether acrylate (EGPEA), poly(ethylene glycol phenyl ether acrylate) (polyEGPEA), phenyl methacrylate, 2-ethylphenoxy methacrylate, 2-ethylphenoxy acrylate, hexylphenoxy methacrylate, hexylphenoxy acrylate, benzyl methacrylate, 2-phenylethyl methacrylate, 4-methylphenyl methacrylate, 4-methylbenzyl methacrylate, 2-2-methyphenylethyl methacrylate, 2-3-methylphenylethyl methacrylate. 2-4-methylphenylethyl methacrylate, 2-(4-propylphenyl)ethyl methacrylate, 2-(4-(1-methylethyl)pheny)ethyl methacrylate, 2-(4-methoxyphenyl)ethylmethacrylate, 2-(4-cyclohexylpheny)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates and acrylates, and including mix thereof. Other aryl acrylate monomers and aryl methacrylate monomers are likely to occur to one skilled in this art in light of the present disclosure. EGPEA and polyEGPEA are preferred.

The first monomeric component should be added to the composition in an amount sufficient to provide high refractive index, a moderate water uptake, and enhanced backbone rigidity. Preferably, the first monomeric component comprises at least about 10 weight percent of the composition; more preferably, at least about 20 weight percent; most preferably, at least about 30 weight percent. The first monomeric component should be added in an amount to avoid an undesirably low glass transition temperature in the resulting copolymer. Preferably, the first monomeric component comprises less than about 60 weight percent of the composition; more preferably, less than about 50 weight percent; most preferably, less than about 45 weight percent.

The second monomeric component includes a monomer having an aromatic ring with a substituent having at least one site of ethylenic unsaturation. Preferably, this second monomeric component is not an acrylate. Such monomers correspond to the general formula (II):

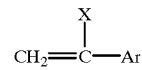

where X is —H or —CH₃, and Ar is a substituted or unsubstituted aromatic ring.

Representative second monomeric components include, for example, substituted and unsubstituted styrene compounds. These compounds may be substituted with hydrogen, halogen (e.g. Br, Cl, F), lower alkyl groups (e.g. methyl, ethyl, propyl, butyl, isopropyl), and/or lower alkoxy groups. Monomers containing acrylic or acrylamide bridges should be avoided. Suitable aromatic monomers include, for example: styrene, methoxy styrene, and chlorostyrene. Styrene and chlorostyrene are preferred. Styrene is most preferred.

The second monomeric component should be added in an amount sufficient to increase the glass transition temperature of the resulting copolymer to a desired working temperature. The second monomeric component is believed to provide a higher refractive index via the aromatic ring, hydrophobocity, and a higher glass transition temperature. Preferably, the second monomeric component comprises at least about 10 weight percent of the composition; more preferably, at least about 15 weight percent; most preferably, at least about 20 weight percent. The second monomeric component should be added in an amount less than that at which the refractive index, optical clarity, or other desirable properties of the copolymer are adversely affected. Preferably, the second monomeric component comprises less than about 60 weight percent of the composition; more preferably, less than about 40 weight percent; most preferably, less than about 30 weight percent.

The third monomeric component comprises a high water content hydrogel-forming monomer. Preferably, the third monomeric component includes a methacrylate without an aromatic substituent. Suitable high water content hydrogel-forming monomers include, for example: hydroxyethyl methacrylate (HEMA), hydroxyetboxyethyl methacrylate (HEEMA), hydroxydiethoxyethyl methacrylate, methoxyethyl methacrylate, methoxyethoxyethyl methacrylate, methoxydiethoxyethyl methacrylate, ethylene glycol dimethacrylate, n-vinyl-2-pyrrolidone, methacrylic acid, vinyl acetate and the like and mixtures thereof. One skilled in this art will recognize that many other high water content hydrogel-forming monomers are likely to be operable in view of this disclosure. HEMA and HEEMA are preferred.

The third monomeric component is desirably added in an amount sufficient to render the resulting copolymer hydratable. Preferably, the third monomeric component comprises at least about 10 weight percent of the composition; more preferably, at least about 20 weight percent; most preferably, at least about 25 weight percent. The third monomeric component should be added in an amount low enough to avoid statistically significant expansion upon hydrating the copolymer. Preferably, the third monomeric component comprises less than about 60 weight percent of the composition; more preferably, less than about 50 weight percent; most preferably, less than about 40 weight percent.

The copolymer may also include a crosslinking agent. The copolymerizable crosslinking agent(s) useful in forming the copolymeric material of the invention include any terminally ethylenically unsaturated compound having more than one unsaturated group. Preferably, the crosslinking agent includes a diacrylate or a dimethacrylate. The crosslinking agent may also include compounds having at least two (meth)acrylate and/or vinyl groups. Particularly preferred crosslinking agents include diacrylate compounds represented by the following formula (III):

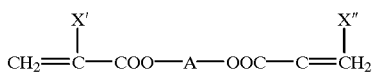

wherein X' and X" separately and independently represent a hydrogen atom or a methyl group; and A represents a substituted or unsubstituted divalent hydrocarbyl group. In a preferred form of formula (III), A represents a substituted or unsubstituted divalent aliphatic radical, and preferably a 1–6 carbon alkylene.

Representative crosslinking agents include, for example: diacrylate compounds including ethylene glycol dimethacrylate (EGDM), diethylene glycol dimethacrylate, polyethylene glycol dimethacrylate, alkyl methacrylate, 1-3-propanedioldimethacrylate allymethacrylate, 1,6-hexanediol dimethacrylate, 1,3-butanediol dimethacrylate, 1,4-butanediol dimethacrylate as well as, divinyl compounds including divinyl hydrocarbons and divinyl benzene, and the like. Ethylene glycol dimethacrylate is preferred.

The crosslinking agent should be added in an amount sufficient to permit the hydrated copolymer to return to its original shape after being folded. Preferably, the crosslinking agent comprises at least about 1 weight percent of the composition; more preferably, at least about 3 weight percent. Conversely, the crosslinking agent should be added in an amount low enough avoid making the copolymer too rigid or brittle. Preferably, the crosslinking agent comprises less than about 10 weight percent of the composition, more preferably, less than about 5 weight percent.

One skilled in the art will appreciate that additives such as ultraviolet (UV) blocking agents, colorants, etc. optionally may be added to the polymer of this invention depending upon the intended application. Representative UV absorbing materials include those disclosed, for example, in column 5, lines 3–29 of U.S. Pat. No. 5,433,746 to Namdaran et al., which is herein incorporated by reference. Suitable UV absorbers include, for example, benzophenone, vinyl benzophenone, and benzotriazole. When employed, the UV absorbing material is preferably added in a concentration less than about 1 percent based on the total weight of the composition.

The copolymers of the invention may be produced using conventional polymerization techniques. For example, the monomers can be blended together and heated to an elevated temperature to facilitate the polymerization reaction. Catalysts and/or initiators, for example, selected from materials well know for such use in the polymerization art, may be included in the monomer mix in order to promote, and/or increase the rate of, the polymerization reaction. Representative initiators include free radical initiators such as 2-2'-azobisisobutyronitrile (AIBN), benzoyl peroxide, acetyl peroxide, lauryl peroxide, t-butyl peroxide, and the like and mixtures thereof. 2-2'-azobisisobutyronitrile (AIBN) is preferred.

Method

Turning now to the method of manufacturing ophthalmic devices from the copolymer, the method entails the following general steps. A rigid, hydratable copolymer is provided which is derived from a mixture of first, second, and third monomeric components as described herein. The copolymer has a glass transition temperature greater than about normal room temperature, and has a refractive index greater than about 1.55. The rigid copolymer is then formed into a rigid ophthalmic device having the desired dimensions. The copolymer is then hydrated to form a foldable hydrated ophthalmic device. Preferably, the hydrated copolymer has an equilibrium water concentration less than about 10 weight percent, and a refractive index greater than about 1.55.

More specifically, the copolymer of the present invention is typically formed in the shape of sheet or rod. A rigid ophthalmic device is generally formed by cutting the device, such as from a rigid sheet of the copolymer, and polishing the device. The ophthalmic devices of the desired dimension and diopter may be cut from the rigid copolymer sheet using customary lathe cutting techniques at room temperature. Similarly, the devices can be polished using customary polishing techniques, such as tumble polishing. The ophthalmic device is preferably an IOL.

The resulting ophthalmic device is then hydrated. This may be achieved by soaking the ophthalmic device in an aqueous solution (such as water or saline), preferably at an elevated temperature (e.g. between 20–100° C.), for sufficient time to inculcate the device with water (e.g. for a time period of from several minutes to several hours or longer).

An ophthalmic or other device fabricated from a polymer of the present invention does not significantly expand or change shape when hydrated. In other words, there is no statistically significant difference between the diameter and thickness of the dry device and that of the hydrated device. Thus, for IOLs, the rigid intraocular lens and the foldable hydrated intraocular lens have essentially the same dimensions.

Copolymer Properties

The copolymers of the invention have a unique combination of desirable characteristics, for example, high refractive index, good mechanical properties, high glass transition temperature, optical clarity, hydratability, and foldability once hydrated.

A particularly advantageous combination of properties includes having a copolymer which is foldable at room temperature despite having a glass transition temperature above room temperature, and which also has a refractive index (RI) greater than about 1.50. Because the refractive index of the hydrated copolymer tends to be greater than 1.50 (and the preferred copolymers have a refractive index greater than about 1.55), the copolymers are especially attractive for ophthalmic applications such as intraocular lenses. The refractive power of a lens is a function of its shape and the refractive index of the material of which it is made. A lens made from a material having a higher refractive index can be thinner and provide the same refractive power as a lens made from a material having a relatively lower refractive index. Thinner lenses are easier to insert and cause less trauma during surgery. Thus, in general, the higher the refractive index, the better the material with other factors remaining the same. RIs of at least 1.558 have been attained.

The mechanical properties of the copolymer, such as the glass transition temperature, permit it to be cut and polished (i.e., machined) at room temperature (rather than molded, or shaped at cryogenic temperatures). The copolymer is rigid at normal room temperature when dry, and flexible at normal room temperature when hydrated. In other words, the dry copolymer is rigid or solid enough at room temperature to be workable by conventional cutting or lathing; and the hydrated copolymer is flexible enough at room temperature that it can bend 180 degrees without cracking. Beneficially, the dry copolymer is also not very brittle.

The ability to cut and polish an ophthalmic device facilitates forming a lens having the minimum central thickness allowed by the refractive index of the material. Thus, a thinner lens is obtainable from the copolymer of the invention than from material having the same refractive index that must be molded. For example, a 20 diopter lens may be produced having a central thickness less than about 0.4 mm. The thinness in turn permits the copolymer to be injected through an incision as thin as about 1 mm or less. This provides a significant advancement in the field of ophthalmic surgery in which much larger incisions are customary.

Regarding the glass transition temperature (Tg) of the copolymer, the Tg is preferably greater than about normal room temperature so that it is workable by conventional cutting and lathing techniques. Preferably, the Tg is greater than about 20° C., more preferably greater than about 25° C., and most preferably, greater than about 30° C. Suitable ophthalmic devices made of copolymers having glass transition temperatures greater than about normal body temperature may also be obtained. Differential scanning calorimetry (DSC) provides a method of measuring Tg.

As discussed, the copolymer of the invention becomes flexible when hydrated. The hydrating process allows a highly efficient distribution of water molecules throughout the structure of the IOLs to make the hard polymer soft and foldable with minimal water uptake. The hydrated copolymer has an equilibrium water content (EWC) less than about 10 weight percent. Preferably, the EWC is less than about 8% by weight, more preferably less than about 5%, and most preferably, less than about 4% by weight. Such low water uptake allows efficient hydration without adversely affecting mechanical or optical properties of the foldable lens. For example, neither lens dimensions nor refractive index change significantly upon hydration. Regarding expansion upon hydration, the copolymers of the invention tend to expand less than about 10 volume percent when compared to the unhydrated copolymer; preferably, the volume percent expansion upon hydration is less than about 5%. Expansion percent is calculated by measuring the difference in dimension of standard buttons before and after hydration.

Thus, the copolymer of the invention exhibits a desirable and unique combination of properties including machinability when unhydrated, and minimal expansion upon hydration; the copolymer also has a relatively high refractive index.

Surgical Method

Employing the copolymer of the invention, cataract surgery may be carried out through an incision of 1.5 mm or less. After applying topical anesthesia to the eye, an IOL made of the new copolymer material may be injected into the eye. No sutures are necessary in this process.

A method of implanting an ophthalmic device within an eye may be carried out by providing a hydratable ophthalmic device which is rigid at room temperature when dry, and foldable at room temperature when hydrated. The ophthalmic device is hydrated and a syringe is provided which contains the hydrated ophthalmic device. The ophthalmic device, which is preferably an intraocular lens made of the copolymer of the invention, is then injected into the eye. Desirably, the ophthalmic device is injected into the eye through an incision less than about 1.5 mm in length.

The lens may be inserted using a device, for example, like that described in U.S. Pat. No. 4,715,373 to Mazzocco, which is herein fully incorporated by reference. The shape or fixation system used to position the IOL in the eye is not critical to this invention. The copolymers may be used in a foldable lens having a variety of fixation systems. See, for example, U.S. Pat. No. 5,776,191 to Mazzocco, which is herein fully incorporated by reference, for a discussion regarding fixation systems for IOL structures.

EXAMPLES

Example 1

Various copolymers are prepared by mixing the following ingredients under reduced pressure: a first, second and third monomeric component, a crosslinker and a polymerizable UV blocking agent. Vinyl benzotriazole at a total concentration of 0.3% by weight is utilized as the UV blocking agent. To initiate polymerization a free radical initiator 2-2'-azobisisobutyronitrile (AIBN) is employed at concentration of 0.2% by weight. The monomer solution is mixed in a glass flask using a magnetic stir bar for 30 minutes. The solution is then filtered through a 0.2 micron ($\mu$) filter and injected into a sheet mold comprising two glass plates held together with spring clips and separated by a plastic gasket. The mold is then placed in a water bath for 10 hours at 60° C., then removed and post cured at 95° C. in oven for 12 hours. A clear, bard polymer sheet is obtained.

Intraocular lenses of various diopters (5, 10, 20, and 34) are cut from the rigid plastic sheet using conventional machining techniques as used to manufacture polymethylmethacrylate (PMMA) IOLs.

The IOLs are tumble polished for 2 days at 20° C. The polished lenses are rinsed with ultra-pure water. At this stage the IOLs are still hard and non-foldable. The IOLs are then placed in individual vials filled with saline solution. The vials are placed in a temperature controlled oven and subjected to the following conditioning cycle: increase temperature from 20° C. to 40° C. at a rate of 10 degree C. per hour. Hold at 40° C. for 30 minutes. Increase temperature from 40° C. to 60° C. at a rate of 10 degree C. per hour. Hold at 60° C. for 4 hours. Decrease temperature from 60° C. to room temperature (approximately 20° C.) at 10 degree C per hour. The IOLs were soft and easily foldable and had excellent optical properties. Lens dimensions (optic size, thickness, diameter) did not change significantly with hydration. The surface and edges of the samples were found to be very smooth.

The equilibrium water content was measured after hydration using gravimetric analysis. The refractive index and glass transition temperature of the lenses was also measured. The results are shown in Table 1.

TABLE 1

| Formulation | 1st Monomer | 2nd Monomer | 3rd Monomer | Cross-linker | EWC (Weight %) | Machinability | Foldability | RI (hydrated) | Expansion % |
|---|---|---|---|---|---|---|---|---|---|
| 1 | 40% EGPEA | 26% styrene | 30% HEMA | 4% EGDM | 4 | Good | Fair | 1.551 | 1.5 |
| 2 | 35% EGPEA | 26% styrene | 35% HEEMA | 4% EGDM | 3.8 | Good | Fair | 1.551 | 1.5 |
| 3 | 40% poly EGPEA | 20% chlorostyrene | 36% HEMA | 4% EGDM | 3.5 | Fair | Poor | 1.552 | 1.3 |
| 4 | 43% EGPEA | 26% styrene | 27% methacrylic acid | 4% EGDM | 4.1 | Good | Fair | 1.551 | 1.8 |
| 5 | 25% poly EGPEA | 11% styrene | 60% HEMA | 4% EGDM | 12.1 | Fair | Fair | 1.523 | 5.8 |
| 6 | 40% poly EGPEA | 26% styrene | 30% HEMA | 4% EGDM | 4.0 | Good | Good | 1.551 | 0.1 |
| 7 | 45% poly EGPEA | 31% styrene | 20% HEMA | 4% EGDM | 1.3 | Good | Poor | 1.556 | 0.1 |
| 8 | 50% poly EGPEA | 36% styrene | 10% HEMA | 4% EGDM | 1.1 | Good | Poor | 1.554 | 0.1 |
| 9 | 25% poly EGPEA | 11% styrene | 60% HEEMA | 4% EGDM | 16.5 | Poor | Fair | 1.509 | 7.2 |
| 10 | 40% poly EGPEA | 26% styrene | 30% HEEMA | 4% EGDM | 9.2 | Poor | Fair | 1.514 | 6.5 |
| 11 | 45% poly EGPEA | 31% styrene | 20% HEEMA | 4% EGDM | 4.6 | Poor | Fair | 1.533 | 2.3 |
| 12 | 50% poly EGPEA | 36% styrene | 10% HEEMA | 4% EGDM | 5.3 | Poor | Fair | 1.541 | 3.6 |
| 13 | 40% poly EGPEA | 28% styrene | 30% HEMA | 2% EGDM | 5.1 | Fair | Good | 1.551 | 0.3 |
| 14 | 34% poly EGPEA | 31% styrene | 32% HEMA | 3% EGDM | 5.0 | Fair | Fair | 1.553 | 0.4 |
| 15 | 41% poly EGPEA | 26% styrene | 31% HEMA | 2% EGDM | 4.5 | Poor | Fair | 1.552 | 3.1 |
| 16 | 41% poly EGPEA | 27% styrene | 31% HEMA | 1% EGDM | 4.8 | Poor | Fair | 1.549 | 4.6 |
| 17 | 20% poly EGPEA | 40% styrene | 40% HEMA | 1% EGDM | 3.2 | Good | Poor | 1.551 | 2.1 |
| 18 | 41% poly EGPEA | 27% chlorostyrene | 31% HEMA | 1% EGDM | 5.1 | Fair | Fair | 1.547 | 2.1 |
| 19 | 40% poly EGPEA | 26% chlorostyrene | 30% HEMA | 4% EGDM | 4.2 | Fair | Fair | 1.551 | 0.2 |

HEMA = hydroxyethyl methacrylate
HEEMA = hydroxyethoxyethyl methacrylate
EGPEA = ethylene glycol phenylether acrylate
EGDM = ethylene glycol dimethacrylate

| Comparative Material | EWC (Weight %) | RI | Machinability | Foldability After Hydration | Expansion % |
|---|---|---|---|---|---|
| Hydrogel 1 | 60 | 1.38 | Good | Good | 15 |
| Hydrogel 2 | 30 | 1.44 | Good | Good | 11 |
| Hydrogel 3 | 75 | 1.34 | Good | Good | 25 |
| Hydrogel 4 | 20 | 1.46 | Good | Good | 10 |
| Acrylic 1 | 0 | 1.54 | Not Machinable | — | 0 |
| Acrylic 2 | 0 | 1.55 | Not Machinable | — | 0 |

Hydrogel 1 = poly HEMA
Hydrogel 2 = poly (HEMA-co-MMA)
MMA = methyl methacrylate
Hydrogel 3 = poly (HEMA-co-NVP)
NVP = n-vinyl pyrrolidone
Hydrogel 4 = highly crosslinked poly (HEMA-co-MMA)
Acrylic 1 = phenylethyl acrylate 79 weight %
methylmethacrylate 16 weight %
EGDM 5 weight %
Acrylic 2 = 2-phenoxyethyl acrylate 88 weight %
n-hexyl acrylate 10 weight %
EGDM 2 weight %

In the above table, "machinability" refers to cutting the unhydrated material with a lathe in which a diamond tool comes in contact with the material while rotating at high speed. Good machinability means the material cuts cleanly into disks so the radii and dimensions of the final product may be selected in advance. Fair machinability means the material can be machined if environmental parameters can be controlled, for example, by decreasing the temperature. Poor machinability means the material tends to deform or break when lathe cut, but it is still machinable if environmental parameters are controlled. Not machinable means the material cannot be cut with a lathe and must be formed using methods such as molding. "Foldability" refers to the ability to bend the material as much as about 180° without breaking once the material has been hydrated. Good foldability means the material can be easily folded using forceps when the material is cut into a disk about the size of a standard lens. Fair foldability means a hydrated disk of the material folds when applying little force. Poor foldability means the hydrated disk folds without breaking when a greater force is applied.

Example 2

A hydration study was conducted to assess the change in dimension after complete hydration. Twenty samples of each formulation described in Example 1 were used. Samples consisted of disks 16.5 mm in diameter and 2.0 mm in thickness. The results were averaged for each formulation.

| Formulation | % Change in Diameter | % Change in Thickness |
|---|---|---|
| 1 | 0.02 ± 0.01 | 0.04 ± 0.01 |
| 2 | 0.05 ± 0.02 | 0.08 ± 0.02 |
| 3 | 0.06 ± 0.01 | 0.08 ± 0.01 |
| 4 | 0.08 ± 0.03 | 0.06 ± 0.01 |

There were no significant dimensional changes after hydration.

What is claimed is:

1. An ophthalmic device comprising a hydratable copolymer, the copolymer comprising:
    a) at least about 20 weight percent of a first monomeric component selected from the group consisting of ethylene glycol phenyl ether acrylate, and polyethylene glycol phenyl ether acrylate;
    b) at least about 10 weight percent of a second monomeric component selected from the group consisting of substituted styrene and unsubstituted styrene;
    c) at least about 10 weight percent of a third monomeric component selected from the group consisting of hydroxy ethyl methacrylate, hydroxyethoxy ethyl methacrylate, and methacrylic acid;
    d) less than about 10 weight percent of a crosslinking agent selected from the group consisting of a diacrylate and a dimethacrylate, wherein the copolymer has a refractive index greater than about 1.50 and is foldable at normal room temperature when hydrated; and
    (e) wherein the copolymer has a refractive index greater than about 1.5 and is rigid at about room temperature when dry, and wherein the copolymer is foldable at about room temperature when hydrated, and is machinable at about room temperature when dry.

2. The ophthalmic device of claim 1 wherein the ophthalmic device is an intraocular lens.

* * * * *